(12) United States Patent
Langlois et al.

(10) Patent No.: US 6,348,436 B1
(45) Date of Patent: Feb. 19, 2002

(54) FLUID COMPRISING CELLULOSE NANOFIBRILS AND ITS USE FOR OIL MINING

(75) Inventors: Bruno Langlois, Des Bois; Joël Benchimol, Francqueville; Gilles Guerin, Eaubonne; Isabelle Vincent, Evreux; Alain Senechal, Charenton; Robert Cantiani, Lyon, all of (FR)

(73) Assignee: Rhodia Chimie, Cedex (FR)

( * ) Notice: Subject to any disclaimer, the term of this patent is extended or adjusted under 35 U.S.C. 154(b) by 0 days.

(21) Appl. No.: 09/214,769

(22) PCT Filed: Jul. 11, 1997

(86) PCT No.: PCT/FR97/01297

§ 371 Date: May 14, 1999

§ 102(e) Date: May 14, 1999

(87) PCT Pub. No.: WO98/02499

PCT Pub. Date: Jan. 22, 1998

(30) Foreign Application Priority Data

| Jul. 15, 1996 | (FR) | ............ 96/09061 |
| Jul. 15, 1996 | (FR) | ............ 96/09062 |
| Aug. 2, 1996 | (FR) | ............ 96/09944 |
| Sep. 27, 1996 | (FR) | ............ 96/11779 |
| Sep. 27, 1996 | (FR) | ............ 96/11986 |

(51) Int. Cl.$^7$ ............ C09K 7/00; C09K 7/02
(52) U.S. Cl. ............ 507/112; 507/104
(58) Field of Search ............ 507/112, 104

(56) References Cited

U.S. PATENT DOCUMENTS

| 4,629,575 A | * | 12/1986 | Weibel | ............ 507/111 |
| 5,362,713 A | * | 11/1994 | Westland et al. | ............ 507/110 |
| 5,385,640 A | * | 1/1995 | Weibel | ............ 162/23 |
| 5,487,419 A | * | 1/1996 | Weibel | ............ 162/9 |
| 5,964,983 A | * | 10/1999 | Dinand et al. | ............ 162/27 |

FOREIGN PATENT DOCUMENTS

EP 726356 * 8/1996

\* cited by examiner

*Primary Examiner*—Philip Tucker
(74) *Attorney, Agent, or Firm*—Jean-Louis Seugnet

(57) ABSTRACT

The present invention relates to a drilling fluid comprising cellulose nanofibrils comprising at least 80% of cells with primary walls and charged with carboxylic acids and with acidic polysaccharides, alone or as a mixture. This additive, alone, gives the drilling fluid shear-thinning properties and is stable up to temperatures of about 180° C.

18 Claims, No Drawings

FLUID COMPRISING CELLULOSE NANOFIBRILS AND ITS USE FOR OIL MINING

This application is an application under 35 U.S.C. Section 371 of International Application Number PCT/FR97/01297 filed on Jul. 11, 1997.

The present invention relates to fluids used in the presence of water, which are applied in the field of petroleum extraction, either for the operations for installing wells, with the drilling operations, the so-called "work-over" operations and the completion operations, or for the actual exploitation of the petroleum deposit.

Drilling operations consist in drilling a hole using a tungsten carbide drill bit in particular, fixed to hollow drillpipes screwed end-to-end. Usually, mud comprising additives in aqueous solution is injected into the drillpipe string. This mud then rises via the probe hole, outside the drillpipes, and entrains components of rocks detached during the drilling operation. At the same time, the rock-laden mud establishes a counterpressure which consolidates the hole. The mud is then extracted from the drilling hole in order to be freed of the rocks it contains, before being reinjected into the hollow drillpipes.

Under such working conditions, it is essential that the additives added to the mud give it specific rheological behaviour. The reason for this is that when it is subjected to very high shear stresses and high temperatures, as is the case on the drill bit, the fluid must be of sufficiently low viscosity to facilitate its evacuation out of the hollow drillpipes. On the other hand, this same fluid, laden with rocks, must have a viscosity which is high enough to keep in suspension the cuttings entrained during the drilling.

The use of high molecular weight polysaccharides, for example such as xanthan gum, as an additive for drilling muds or fluids in order to give the said fluid the specific type of rheological behaviour described above, which is referred to as shear-thinning behaviour, is well known.

However, although xanthan gum has undeniable advantages in this type of application, it nevertheless remains limited since the rheological properties of the drilling fluid degrade over time, and this occurs all the more quickly when the temperature to which it is subjected is in the region of or exceeds 120° C. Now, in petroleum drilling operations, it is quite common for such temperatures to be reached. Firstly, there is considerable heating of the mud caused by the movement of the drill bit. Furthermore, the depth of the deposit and its geographical location (hot well) also have consequences on the temperature to which the fluid is subjected. Thus, temperatures of this order of magnitude can be reached without difficulty at the bottom of the well since the depth reached during the drilling operations is in the region of a kilometre or more. In addition, there are wells in which the temperature of the earth's crust is already at a higher level than elsewhere (hot wells) which further accentuates the effect of the increase in the temperature of the subsoil as the depth increases.

In a normal cycle, the effect caused by such temperatures is not systematically detrimental, or at any rate not at the start of use of the additive, since the duration for which the fluid is at these high temperatures is limited. However, it should be appreciated that it is not rare to have to stop the drilling operations in order to replace one of the tools, for example the drill bit. Now, in such a case, the drilling fluid remains under high temperature conditions for a relatively long period.

When the fluid is subjected to high temperatures, its viscosity degrades considerably and the role of suspending the cuttings torn out during the drilling operation is no longer maintained. This may thus be one of the causes of a blockage of the well by deposition of rocks at the bottom of it.

European patent application EP 134,084 describes the use of cellulose microfibrils as an additive for a petroleum drilling fluid. However, although the heat resistance of this additive is better than that of xanthan gum, it nevertheless remains limited to 160° C. when it is used as sole viscosifying agent.

The aim of the present invention is thus to propose a drilling fluid additive which has better thermal stability than the polysaccharides employed, better thermal stability than the cellulose microfibrils discussed above, while at the same time retaining the advantages of these microfibrils.

Thus, the object of the present invention is to propose a fluid comprising a compound which can give the said fluid quite specific flow behaviour.

In addition, on account of its improved heat stability, the additive according to the invention makes it possible for the fluid to conserve these rheological properties, even at very high temperatures, i.e. at least equal to 180° C., or even up to 200° C.

Moreover, the additive according to the invention is stable in aqueous media comprising salts or additives of any other type commonly used in this type of application for controlling or adapting the fluid characteristics, such as oxygen scavengers, filtrate reducing agents, rheology modifiers, such as fillers and soluble or insoluble weighting materials.

In addition, the additive used according to the invention has the characteristic of conserving its particular viscosifying properties over a very wide water composition range, thus making it suitable for uses in the presence of highly mineralized waters or sea waters.

The fluid according to the invention is moreover entirely suitable, on account of its stable shear-thinning properties, for uses close to the petroleum production zone, or during deviated drilling operations in which, for reasons of flow and of damage to the formation, the fluids must preferably be formulated with few or no solids.

An additional advantage of the additive according to the invention is that it is easier to filter than polysaccharides of the xanthan gum type, which reduces the risks of damaging the drilling site by avoiding the formation of a plug in the well. Moreover, this can contribute towards making it easier subsequently to process the drilling muds, i.e. to separate out the cuttings, before recycling the muds into the well.

These aims and others are achieved by the present invention, which consists of a petroleum drilling fluid comprising cellulose nanofibrils containing at least about 80% of cells with primary walls and charged with carboxylic acids and with acidic polysaccharides, alone or as a mixture.

However, other advantages and characteristics of the present invention will emerge more clearly on reading the description and the examples which follow.

Before describing the fluid according to the invention, it should be pointed out that this fluid is particularly suitable for use as a drilling fluid.

However, its rheological properties, its filterability and its compatibility with numerous components make it just as suitable for subsequent applications to the actual drilling and/or applications associated with the actual exploitation of the deposit.

Thus, by means of adapting its characteristics, in particular such as the viscosity, the fluid can be used in so-called "work-over" operations. It is similarly possible to use the fluid, again after adapting its rheological characteristics, for the assisted recovery of petroleum.

For reasons of simplicity, mention will only be made in the text hereinbelow of the application of the fluid according to the invention in drilling operations, bearing in mind that the use of such a fluid is not limited to this sole application.

As has been mentioned above, the drilling fluid according to the present invention comprises quite specific cellulose nanofibrils as additive, which, in contrast with the standard microfibrils, such as those described in particular in the abovementioned European patent application, have particularly interesting and surprising advantages.

Thus, the cellulose nanofibrils forming part of the drilling fluid composition contain at least about 80% of cells with primary walls, and are charged, at the surface, with carboxylic acids and with acidic polysaccharides, alone or as a mixture.

The term "carboxylic acids" is intended to refer to simple carboxylic acids and their salts. These acids are preferably chosen from uronic acids or their salts. More particularly, the said uronic acids are galacturonic acid and glucuronic acid, or their salts.

As acidic polysaccharides, mention may be made of pectins, which are more particularly polygalacturonic acids. These acidic polysaccharides can be present as a mixture with hemicelluloses.

As has been mentioned previously, the cellulose nanofibrils used in the drilling fluid are charged with acids and with polysaccharides. It should be noted that the situation here is not one of simple mixing between the said nanofibrils and the acids and polysaccharides, but rather an intimate combination of these two types of compound. The reason for this is that the process for preparing the nanofibrils is such that the acids and polysaccharides are not entirely separated from the fibres, but rather still remain at the surface of these fibres, giving them quite specific properties. Thus, the nanofibrils used according to the invention are charged at the surface with carboxylic acids and acidic polysaccharides, alone or as a mixture. It should be noted that it is not possible to obtain the same properties if these acids and/or polysaccharides are entirely separated from the nanofibrils during their preparation, in order for them to be re-added thereafter.

The cellulose nanofibrils forming part of the composition of the fluid according to the present invention are obtained from cells preferably consisting of at least 80% of primary walls. Preferably, the amount of primary walls is at least 85% by weight.

Such characteristics are present in particular in parenchymal cells. Sugar beet pulp, citrus fruits such as lemons, oranges and grapefruit, and most fruit and vegetables are examples of parenchyma.

Moreover, the cellulose nanofibrils forming part of the composition of the fluid according to the invention are essentially amorphous.

The term "essentially amorphous" is intended to refer to nanofibrils in which the degree of crystallinity is less than or equal to 50%. According to a specific variant of the present invention, the degree of crystallinity is between 15 and 50%. Preferably, the degree of crystallinity is less than 50%.

The cellulose nanofibrils moreover have a cross-section of between about 2 and about 10 nm. More particularly, the nanofibril cross-section is between about 2 and about 4 nm.

The specific nanofibrils forming part of the composition of the drilling fluids according to the invention have such characteristics on account of the use of a quite specific preparation process, which will now be described.

It should be noted that this process has been described in patent application EP 726,356, to which reference may be made for further details.

Firstly, the said process is more particularly carried out on the pulp of vegetables with primary walls, such as, for example, beetroot pulp, after it has undergone a preliminary step of extraction of the sucrose, according to the methods known in the art.

The preparation process comprises the following steps:
(a) first acidic or basic extraction, after which a first solid residue is recovered,
(b) optionally, second extraction, carried out under alkaline conditions, of the first solid residue, after which a second solid residue is recovered,
(c) washing of the first or second solid residue,
(d) optionally, bleaching of the washed residue,
(e) dilution of the third solid residue obtained after step (d) so as to obtain a solids content of between 2 and 10% by weight,
(f) homogenization of the dilute suspension.

In step (a), the term "pulp" is intended to refer to wet, dehydrated pulp stored by ensilage or partially depectinized.

The extraction step (a) can be carried out in acidic medium or in basic medium.

For an acidic extraction, the pulp is suspended in an aqueous solution for a few minutes so as to homogenize the acidified suspension at a pH of between 1 and 3, preferably between 1.5 and 2.5.

This operation is carried out with a concentrated solution of an acid such as hydrochloric acid or sulphuric acid.

This step may be advantageous for removing the calcium oxalate crystals which may be present in the pulp, and which, on account of their highly abrasive nature, can cause difficulties in the homogenization step.

For a basic extraction, the pulp is added to an alkaline solution of a base, for example sodium hydroxide or potassium hydroxide, with a concentration of less than 9% by weight, more particularly less than 6% by weight. Preferably, the concentration of the base is between 1 and 2% by weight.

A small amount of a water-soluble antioxidant, such as sodium sulphite $Na_2SO_3$, may be added in order to limit the oxidation reactions of the cellulose.

Step (a) is generally carried out at a temperature of between about 60° C. and 100° C., preferably between about 70° C. and about 95° C.

The duration of step (a) is between about 1 hour and about 4 hours.

During step (a), partial hydrolysis takes place with release and solubilization of most of the pectins and hemicelluloses, while at the same time retaining the molecular mass of the cellulose.

The solid residue is recovered from the suspension obtained from step (a) by carrying out known methods. Thus, it is possible to separate the solid residue by centrifugation, by filtration under vacuum or under pressure, with filter gauzes or filter presses, for example, or else by evaporation.

The first solid residue obtained is optionally subjected to a second extraction step carried out under alkaline conditions.

A second extraction step is carried out when the first step has been carried out under acidic conditions. If the first extraction has been carried out under alkaline conditions, the second step is optional.

According to the process, this second extraction is carried out with a base preferably chosen from sodium hydroxide and potassium hydroxide, whose concentration is less than about 9% by weight, preferably between about 1% and about 6% by weight.

The duration of the alkaline extraction step is between about 1 and about 4 hours. It is preferably equal to about 2 hours.

After this second extraction, if it is carried out, a second solid residue is recovered.

In step (c), the residue derived from step (a) or (b) is washed thoroughly with water in order to recover the residue of cellulosic material.

The cellulosic material from step (c) is then optionally bleached, in step (d), according to the standard methods. For example, a treatment with sodium chlorite, with sodium hypochlorite or with hydrogen peroxide in a proportion of 5–20% relative to the amount of solids treated can be carried out.

Different concentrations of bleaching agent can be used, at temperatures of between about 18° C. and about 80° C., preferably between about 50° C. and about 70° C.

The duration of this step (d) is between about 1 hour and about 4 hours, preferably between about 1 hour and about 2 hours.

A cellulosic material containing between 85 and 95% by weight of cellulose is thus obtained.

After this bleaching step, it may be preferable to wash the cellulose thoroughly with water.

The resulting suspension, which has optionally been bleached, is then rediluted in water to a proportion of 2 to 10% solids, before undergoing a homogenization step.

The homogenization step corresponds to a mixing or blending operation or any operation of high mechanical shear, followed by one or more passages of the cell suspension through an orifice of small diameter, subjecting the suspension to a pressure drop of at least 20 MPa and to a high-speed shear action, followed by a high-speed deceleration impact.

The mixing or blending is carried out, for example, by passage(s) through the mixer or blender for a period ranging from a few minutes to about an hour, in a machine such as a Waring Blendor fitted with a four-blade impeller or a pan mill mixer or any other type of blender, such as a colloidal mill.

The actual homogenization will advantageously be carried out in a homogenizer such as a Manton Gaulin in which the suspension is subjected to a shear action at high speed and pressure in a narrow passage and against an impact ring. Mention may also be made of the Micro Fluidizer, which is a homogenizer mainly consisting of a compressed-air motor which creates very high pressures, an interaction chamber in which the homogenization operation takes place (elongational shear, impacts and cavitations) and of a low-pressure chamber which allows depressurization of the dispersion.

The suspension is introduced into the homogenizer preferably after preheating to a temperature of between 40 and 120° C., preferably between 85 and 95° C.

The temperature of the homogenization operation is maintained between 95 and 120° C., preferably above 100° C.

The suspension in the homogenizer is subjected to pressures of between 20 and 100 MPa and preferably above 50 MPa.

Homogenization of the cellulosic suspension is obtained by a number of passages which can range between 1 and 20, preferably between 2 and 5, until a stable suspension is obtained.

The homogenization operation can advantageously be followed by a high mechanical shear operation, for example in a machine such as the Sylverson Ultra Turrax.

The process which has just been described makes it possible to obtain nanofibrils which further conserve at their surface carboxylic acids and/or polysaccharides, which are one of the reasons for their quite specific properties of heat resistance, and without the use of an additional viscosifying additive.

According to a first variant, the nanofibrils are used in the form of a suspension which has not undergone drying after they have been obtained.

According to a second variant, a cellulose nanofibril composition is used which is obtained from the drying of a nanofibril dispersion in the presence of an additive and optionally of a co-additive. It may likewise be envisaged to use a dispersion of such a composition in the drilling fluids.

Such compositions have in particular been the subject of the following patent applications: FR 96/09061 of 15/07/96, FR 96/11986 of 27/09/96, FR 96/09062 of 15/07/96 and FR 96/11779 of 27/09/96; to which patents reference may be made as regards the nature of the additives, co-additives and preferred combinations, the respective proportions of the additives and co-additives, and the method for preparing them.

According to a first possibility, the nanofibril composition comprises carboxycellulose, preferably carboxymethylcellulose, with a degree of substitution of less than or equal to 0.95, as additive.

These compositions can optionally comprise at least one co-additive chosen from:
 saccharide monomers or oligomers,
 compounds of formula $(R^1R^2N)$ COA, in which formula $R^1$ or $R^2$, which may be identical or different, represent hydrogen or a $C_1$–$C_{10}$, preferably $C_1$–$C_5$, alkyl radical, A represents hydrogen, a $C_1$–$C_{10}$, preferably $C_1$–$C_5$, alkyl radical or alternatively the group $R'^1R'^2N$ with $R'^1$ and $R'^2$, which may be identical or different, representing hydrogen or a $C_1$–$C_{10}$, preferably $C_1$–$C_5$, alkyl radical,
 cationic or amphoteric surfactants, it being possible for these co-additives to be used alone or as a mixture.

A second possibility consists in using compositions comprising the nanofibrils with, as additive, carboxycellulose in salt or acid form, with a degree of substitution of greater than 0.95, a natural polysaccharide, a polyol; it being possible for these additives to be used alone or in combination.

The natural polysaccharide can be of bacterial, animal or plant origin.

Polysaccharides are polymers comprising saccharide units. Preferably, polysaccharides which are in an anionic or nonionic form are used.

Among the anionic polysaccharides which are suitable, mention may be made, without intending to be limited thereto, of xanthan gum, succinoglycans, carrageenans and alginates.

As nonionic polysaccharides, mention may-be made, for example, of galactomannans, for instance guar gum, carob gum, starch and its nonionic derivatives, and nonionic cellulose derivatives.

Among the polyols which are suitable, mention may be made most particularly of polyvinyl alcohol.

The said compositions can optionally also comprise at least one co-additive chosen from one or more of the following compounds:
 carboxycellulose with a degree of substitution of less than or equal to 0.95, preferably carboxymethylcellulose,
 saccharide monomers or oligomers,
 compounds of formula $(R^1R^2N)$ COA, in which formula $R^1$ or $R^2$, which may be identical or different, represent hydrogen or a $C_1$–$C_{10}$, preferably $C_1$–$C_5$, alkyl radical,
A represents hydrogen, a $C_1$–$C_{10}$, preferably $C_1$–$C_5$, alkyl radical or alternatively the group $R'^1R'^2N$ with $R'^1$ and $R'^2$, which may be identical or different, representing hydrogen or a $C_1$–$C_{10}$, preferably $C_1$–$C_5$, alkyl radical, cationic or amphoteric surfactants.

In both possibilities, the content of additive and optionally of co-additive is less than 30% by weight relative to the weight of nanofibrils and of additive and of co-additive.

The process for preparing such nanofibril compositions consists, firstly, in preparing the cellulose nanofibrils from suitable cellulosic pulp by carrying out a hydrolysis, optionally followed by at least one step of bleaching of the pulp thus treated. Everything which has been mentioned previously in this respect remains valid and will not be repeated here.

More particularly, in a first step, at least some of the additive and optionally co-additive(s) are added to the nanofibril suspension, which has optionally undergone at least one homogenization cycle. Next, in a second step, a step of drying of the suspension thus supplemented is carried out.

According to a first variant, the addition of at least some of the additive and optionally co-additive is carried out after the homogenization step.

A first particularly suitable method consists in adding at least some of the additive and optionally co-additive to the suspension after the homogenization step, after this suspension has undergone at least one concentration step.

As a guide, the concentration step(s) take(s) place by filtration, centrifugation or evaporation of some of the water from the suspension, by precipitation, for example in an alcohol, by freezing-thawing, by dialysis, etc.

According to this embodiment, the concentration operation can be carried out until a solids content of about 35% by weight is obtained.

The introduction of the additive and optionally co-additive is carried out in a manner which is known per se, i.e. by any means which allows homogeneous introduction of a solution, a suspension or a powder to a suspension which tends to have the consistency of a paste. For example, mention may be made of blenders, extruders and mixers.

This operation can be carried out over a wide temperature range, more particularly between room temperature and 80° C.

A second method consists in adding at least some of the additive and optionally co-additive to the suspension after the homogenization step, before this suspension has undergone at least one concentration step.

In this case, the concentration step(s) which take(s) place after the addition of additive and optionally of co-additive is (are) carried out in the same way as indicated above.

A third method for carrying out the first variant consists in introducing the additive after the suspension has undergone one or more concentration steps.

According to a second advantageous variant, the introduction of at least some of the additive and optionally co-additive is carried out before or during the homogenization step. When it is indicated that the supplementation takes place during the homogenization step, this means that the additive and optionally the co-additive are introduced when the pulp has undergone at least one cycle of the homogenization step.

The supplementation takes place according to the three methods indicated in the context of the first variant.

Prior to the actual drying step, it may be advantageous to carry out shaping of the suspension which has been concentrated as mentioned previously. This shaping is carried out in a manner which is known to those skilled in the art. Mention may be made in particular, without, however, intending to be limited thereto, of extrusion and granulation.

According to a particularly advantageous variant, the drying step is carried out so as to maintain not less than 3% by weight of water relative to the weight of the solid obtained. More particularly, the weight of water maintained is between 10 and 30% by weight.

The drying advantageously takes place in air, although it may be envisaged to carry it out under an inert gas, such as nitrogen.

It should also be noted that it is preferred to carry out the drying in an atmosphere whose degree of humidity is controlled so as to be able to maintain the desired moisture content in the composition.

The drying temperature should limit any degradation of the carboxylic acids, of the acidic polysaccharides, of the hemicelluloses and/or of the additives and co-additives. It is more particularly between 30 and 80° C., preferably between 30 and 60° C.

It should be noted that it would not constitute a departure from the context of the present invention to carry out a drying operation in several steps, some of which would use the means indicated above for the concentration step.

After the drying step, the composition obtained can be blended.

The composition comprising the nanofibrils, at least one additive and optionally at least one co-additive can be used for the preparation of drilling fluid according to the invention, in this form, but also in the form of a cellulose nanofibril suspension obtained by redispersion of the above-mentioned composition in water or any other medium.

The content of cellulose nanofibrils in the drilling fluid can vary within a wide range. However, it is advantageously between 0.05 and 2% relative to the total weight of the fluid, and preferably between 0.05 and 1%.

It should be noted that the viscosifying effect of the additive according to the invention is more pronounced, for a comparable content, than that of the polysaccharides usually used. Thus, it is possible to reduce the amount of additive without a harmful effect on the Theological properties of the drilling fluid.

Besides the cellulose nanofibrils, the fluid according to the invention can comprise a filtrate-reducing compound. The term "filtrate-reducing compound" is intended to refer to compounds which are adsorbed onto the rocks which form the walls of the well, thereby limiting the diffusion of the various constituent elements of the fluid through the drilling walls.

As examples of compounds of this type, mention may be made, without intending to be limited thereto, of cellulosic compounds, polyacrylamides, high molecular weight polyacrylates, succinoglycans, native starch or its derivatives and charcoal. Among the cellulosic compounds, non-modified or chemically-modified celluloses, for instance carboxymethyl-celluloses, hydroxyethylcelluloses and carboxyethyl-hydroxyethylcelluloses, are compounds which are suitable as filtrate-reducing compounds. Needless to say, there is nothing to prevent these products from being used in combination if the conditions make it necessary.

The amount of filtrate-reducing compound depends greatly on the nature of the rocks passed through. However, as a guide, this is usually between 0 and 1% relative to the total weight of the fluid.

The drilling fluids can also comprise thinning or dispersing agents. Thus, polyphosphates, tannins, lignosulphonates, lignin derivatives, peats and lignites, polyacrylates and polynaphthalene sulphonates can form part of the composition of the drilling fluids, alone or as a mixture.

The amount of thinning or dispersing agent is variable. As a guide, it is between 0 and 1% relative to the total weight of the fluid.

The drilling fluid according to the invention can also comprise an oxygen scavenger. The aim of this type of additive is to trap out the oxygen present in the drilling muds and which can entail degradation of certain additives.

Among the products of this type, mention may be made, for example, of hydroxylamines, hydrazine, sulphites, bisulphites, hydrosulphites and borohydrides.

According to a specific embodiment, hydrazine is used as oxygen scavenger since it does not entail the formation of insoluble precipitates which promote the development of plugs in the well. The hydrazine can be in an anhydrous or hydrated form, in the form of salts such as, for example, chlorides or sulphates, or alternatively in the form of carbohydrazide.

The content of additive of this type generally ranges between 0 and 0.25%.

The drilling fluid according to the invention can also comprise at least one weighting compound and/or at least one mineral colloid.

The weighting components contribute towards maintaining a sufficient hydrostatic pressure in the well and towards maintaining in suspension the rocks entrained during the drilling operation. Such compounds are conventionally chosen from alkaline-earth metal sulphates, silicates or carbonates, for instance barium sulphate, calcium carbonate and potassium and sodium silicates. Alkaline-earth metal or zinc bromides, such as potassium bromide or zinc bromide, can similarly be used. Iron oxides can also be used.

The mineral colloids, which are compounds that are essentially insoluble under the working conditions of the fluid according to the invention, are agents for modifying the rheology of the medium and for maintaining the cuttings in suspension in this medium. Attapulgite, baryta and bentonite, alone or as a mixture, are examples of mineral colloids most commonly used. It should be noted that bentonite, in the presence of a non-saline aqueous medium, also acts as a filtrate-reducing agent.

Although mineral colloids are components which are not always required in the composition of drilling fluids, a particularly advantageous fluid comprises a combination of the cellulose nanofibrils which have been described above with at least one mineral colloid. Bentonite is preferably used.

It should be noted that if the aqueous medium is saline, attapulgite is preferably used as mineral colloid, in combination with the nanofibrils.

The contents of weighting materials and of mineral colloids depend on several factors which are not solely technical. Indeed, although these contents are quite obviously determined as a function of the nature of the soils crossed, the size of the cost generated by the use of these additives is taken into account (presence or absence on site, cost, etc.).

Quite often, and always with the aim of minimizing the costs encountered, the drilling fluid is prepared with the water present at the drilling site.

Thus, it is not uncommon to be in the presence of formation water (in contrast to composition waters, i.e. waters prepared for a specific purpose) charged with salts, for instance sea water, brines or hard waters. In this case, the content of salts in the water used varies according to its origin.

It may, however, arise that the water available is weakly or unladen water. In this case, it may be appropriate to add salts, for example such as chlorides, since, if the rock crossed has a tendency to swell in the presence of water, and to entail problems of plugging during drilling, the presence of salts of this type contributes towards reducing this drawback.

The salts usually used for this purpose are halides, and in particular alkali metal iodides or chlorides, sulphates, carbonates, bicarbonates, phosphates and silicates, alone or as a mixture. Thus, the sodium and potassium salts are among the salts most commonly used.

It is also possible to add, if necessary, inorganic salts in order to promote the precipitation of certain ions, if they are present, and in particular divalent ions. Mention may be made, for example, of the addition of sodium carbonate in order to precipitate calcium, or sodium bicarbonate to precipitate lime, especially when drilling out cement. Mention may also be made of the addition of gypsum or calcium chloride to limit the swelling of clays and the addition of calcium hydroxide or of slaked lime to de-bicarbonate muds contaminated with carbon dioxide.

Here also, the salt content depends on the rocks crossed and on the waters available at the exploitation site, and the operations can be carried out in the presence of salt-saturated fluids.

Fluids whose content of salts of this type is between 0.01 and 2% by weight relative to the drilling fluid can also be used.

One particularly advantageous drilling fluid according to the invention comprises, besides the nanofibrils which have been described previously, at least one inorganic salt chosen from those which have been mentioned previously, or combinations thereof.

Needless to say, the drilling fluid according to the present invention can comprise common additives of the class of high molecular weight polysaccharides, such as xanthan gum or guar, which are useful as viscosifying agents.

Other conventional additives for applications relating to the exploitation of petroleum deposits may form part of the composition of the fluid. Thus, mention may be made of free-radical-transfer agents, for instance lower alcohols, thioureas and hydroquinone; biocides, chelating agents, surfactants, antifoaming agents and anticorrosion agents, for example.

As has been mentioned in the preceding text, the fluid according to the present invention is particularly,suitable for use as a drilling fluid.

In this respect, any type of drilling can be suitable, whether it be vertical, horizontal or slant drilling, such as those which are performed on off-shore platforms.

It should be noted that by virtue of its properties (compatibility with many compounds in particular), the fluid according to the invention does not contaminate cement during "work-over" operations. These operations consist, once the drilling of the well is complete, in introducing a metal case into this well to consolidate it, and then in pouring a cement between this case and the wall of the well.

In addition, by means of adapting the characteristics of the said fluid (rheology, composition), the fluid according to the invention can be used as a spacer fluid, for example.

The fluid according to the invention, again after adapting its composition and its Theological properties, can similarly be used during the actual exploitation of the petroleum deposit, in particular in the assisted recovery of the petroleum. Thus, it can be used as a stimulation fluid, which represents one of the methods developed to increase the yield of the exploitation of a petroleum deposit. Thus, this fluid is introduced into another location in the deposit and, on account of its high viscosity, it allows an additional amount of petroleum to be entrained, thus increasing the yield for the extraction.

Concrete but in no way limiting examples of the invention will now be presented.

EXAMPLE 1

1/ Preparation of the Muds

A mud of the following composition is prepared:

| | |
|---|---|
| Aqueous suspension of bentonite (5%) | 157.50 g |
| Sea water | 140.30 g |
| Filtrate-reducing agent: Drispac modified starch (Drilling Specialties Company) | 0.50 g |
| $NaHCO_3$ | 0.65 g |
| $Na_2CO_3$ | 0.22 g |
| Dispersing agent: polyacrylate colloid 211 (Rhône-Poulenc) | 0.75 g |
| Baryta | 197.20 g |
| Rheological additive in suspension | 66.6 g |

The formulation is prepared such that the amount of rheological additive is 0.28% by weight relative to the aqueous phase.

EXAMPLE (a)

According to the Invention

The Theological additive consists of 66.6 g of a suspension of cellulose nanofibrils, obtained according to Example 20 of European patent application EP 726,356 in the name of Generale Sucriere.

Comparative Example b)

The Theological additive consists of a solution of 66.6 g of xanthan gum (Rhodopol 23P®, Rhône-Poulenc). The solids content of the solution is 1.5%.

The aqueous bentonite suspension is first prepared by hydration for at least 16 hours of a suspension comprising 5% by weight of bentonite in mains water.

The muds a) and b) are prepared in a Hamilton Beach mixer.

The bentonite suspension is thus mixed with sea water and the dissolved Theological additive is then added. The resulting mixture is mixed for 5 minutes, followed by addition of the sodium bicarbonate and then the sodium carbonate and the dispersing agent. This mixture is mixed for 3 minutes. The filtrate-reducing agent is then added, and finally the baryta, and the homogenization operation is continued up to a total mixing time of 25 minutes.

Two muds a) and b) with a density of 1.4 are thus obtained.

2/ Rheological Behaviour of the Muds

The Theological behaviour of the muds is measured after their manufacture and after a treatment at 120° C. in a rolling oven for 24 hours.

In the case of the mud according to the invention, these measurements are also made on the mud which has undergone a treatment similar to that mentioned above but at 140° C.

The measurements are made using a Fann rheometer (Baroid) according to the characteristics indicated in American Petroleum Institute (API) in bulletin 13 D.

These measurements are made at a temperature of 21 ±1° C., by direct reading of the deflection of the torsion wire. The spin speeds are 600, 300, 200 and 100 rpm.

Exploitation of these results makes it possible to define the apparent viscosity of the muds (Va expressed in mPa.s), the plastic viscosity (Vp expressed in mpa.s) and the "Yield point" (Yp expressed in Pa).

It also gives access to the rheological flow profiles of the muds by correspondence, on the one hand, between the spin speeds of the rheometer and the gradients in $s^{-1}$, and the deflections of the torsion wire and the apparent viscosities.

The results are collated in Tables 1 and 2 below:

TABLE 1

| | Mud (a) | Mud a) 120° C. | Mud a) 140° C. | Mud b) | Mud b) 120° C. |
|---|---|---|---|---|---|
| Va (mPa.s) | 47 | 40 | 44 | 34 | 29 |
| Va (mPa.s) | 23 | 19 | 18 | 17 | 20 |
| Yp (Pa) | 23.0 | 20.2 | 25.0 | 16.3 | 8.6 |

From these results, it is seen that, for the same concentration of Theological additive, the apparent viscosity values are higher in the case of the additive according to the invention. This therefore implies that the additive according to the invention has a higher viscosifying power than that of xanthan gum.

Moreover, the higher Yp values obtained with the additive according to the invention show that this additive has greater suspensive properties than those of xanthan gum.

Lastly, it is observed that most of the rheological properties of the mud comprising the additive according to the invention are maintained after a treatment of up to 140° C., in contrast with the conventionally supplemented mud.

TABLE 2

| rate gradient ($s^{-1}$) viscosity (mPa.s) | 1020 | 510 | 340 | 170 | 5.1 |
|---|---|---|---|---|---|
| mud a) | 47 | 72 | 91 | 150 | 1700 |
| mud a) 120° C. | 40 | 61 | 78 | 123 | 1600 |
| mud a) 140° C. | 44 | 70 | 87 | 135 | 1700 |
| mud b) | 34 | 51 | 61 | 93 | 1300 |
| mud b) 120° C. | 29 | 39 | 46 | 69 | 800 |

Calculation of the slope of the logarithmic diagram of the viscosity as a function of the logarithm of the rate gradient shows that a negative slope, of less than −0.5, is obtained for each of the muds, which is characteristic of drilling muds which are suitable for the application, i.e. they have good properties of keeping the cuttings in suspension, thereby avoiding the deposition of these cuttings at the bottom of the well, causing it to become plugged.

It is also confirmed that, at the same concentration and with the same rate gradient, the viscosifying properties of the mud according to the invention are greater than those of the mud comprising xanthan gum as rheological additive.

EXAMPLE 2

This test illustrates the heat stability of the cellulose nanofibrils, used as sole viscosifying agent.

An aqueous suspension of cellulose nanofibrils, obtained according to Example 20 of the abovementioned European patent application EP 96 400 261.2, is prepared at a concentration of 1.68% (i.e. 6 ppb).

The placing in suspension is carried out in accordance with the standard API Section 13 B, using a Hamilton Beach machine, for 30 minutes at slow speed.

The rheological behaviour of the solution is monitored after manufacture and after a heat treatment at 180° C. in an oven, the suspension being placed in a stainless steel cell pressurized with nitrogen, and then rolled for 16 hours.

The viscosities (expressed in mpa.s) are collated in the following table:

TABLE 3

| Gradient ($s^{-1}$) | 1020 | 510 | 340 | 170 | 10.2 | 5.1 |
|---|---|---|---|---|---|---|
| Before treatment | 87 | 130 | 171 | 270 | 1200 | 1800 |
| After treatment | 59 | 95 | 122 | 183 | 900 | 1400 |

It is seen that, under extreme conditions, the additive retains most of its properties and its pseudoplastic nature after a very rigorous heat treatment. Consequently, during the use of this additive in drilling muds, the amount may advantageously remain limited.

NB: the values collated in the above table will be adapted by a person skilled in the art depending on the applications of the fluid. For example, for applications as a drilling fluid, an additive content of less than 1% will preferably be used.

What is claimed is:

1. A drilling fluid used in the presence of water, comprising cellulose nanofibrils containing at least 80% of cells with primary walls and charged with carboxylic acids or with acidic polysaccharides.

2. A drilling fluid according to claim 1, wherein the nanofibrils have at the surface carboxylic acids or acidic polysaccharides.

3. A drilling fluid according to claim 2, wherein the carboxylic acids are unronic acids or their salts, and the polysaccharides are pectins, or a mixture of pectins with hemicelluloses.

4. A drilling fluid used in the presence of water, comprising cellulose nanofibrils containing at least 80% of cells with primary walls and charged with carboxylic acids or with acidic polysaccharides, wherein the content of cellulose nanofibrils is between 0.05 and 2% relative to the total weight of the fluid.

5. A drilling fluid according to claim 4, wherein the content of cellulose nanofibrils is 0.05 to 1%.

6. A drilling fluid used in the presence of water, comprising cellulose nanofibrils containing at least 80% of cells with primary walls and charged with carboxylic acids or with acidic polysaccharides, and a filtrate-reducing agent, in an amount of up to 1% relative to the total weight of the fluid.

7. A drilling fluid according to claim 6, wherein the filtrate-reducing agent is a cellulosic compound, a polyacrylamide, a high molecular weight polyacrylate, a succinoglycan, native starch, or charcoal.

8. A drilling fluid used in the presence of water, comprising cellulose nanofibrils containing at least 80% of cells with primary walls and charged with carboxylic acids or with acidic polysaccharides, and a thinning or dispersing agent in an amount of up to 1% relative to the total weight of the fluid.

9. A drilling fluid according to claim 8, wherein the thinning or dispersing agent is a polyphosphate, a tannin, a lignosulphonate, a peat a lignite, a polyacrylate, or a polynaphtalene sulphonate.

10. A drifting fluid used in the presence of water, comprising cellulose nanofibrils containing at least 80% of cells with primary walls and charged with carboxylic acids or with acidic polysaccharides, and an oxygen scavenger in a content of up to 0.25% relative to the total weight of the fluid.

11. A drilling fluid used in the presence of water, comprising cellulose nanofibrils containing at least 80% of walls with primary walls and charged with carboxylic acids or with acidic polysaccharides, and a weighting compound which is an alkaline-earth metal sulphate, an alkaline-earth metal carbonate, an alkaline-earth metal silicate, an alkaline-earth metal bromide, a zinc bromide, or an iron oxide.

12. A drilling fluid used in the presence of water, comprise cellulose nanofibrils containing at least 80% of cells with primary walls and charged with carboxylic acids or with acidic polysaccharides, and at least one mineral colloid which is attapulgite, baryta, or bentonite.

13. A drilling fluid used in the presence of water, comprising cellulose nanofibrils containing at least 80% of cells with primary walls and charged with carboxylic acids or with acidic polysaccharides, and salts.

14. A drilling fluid according to claim 13, wherein the salts are alkali metal halides, alkali metal sulphates, alkali metal carbonates, alkali metal bicarbonates, alkali metal silicates, or alkali metal phosphates.

15. A drilling fluid according to claim 13, wherein the salt content is between 0.01 and 2% relative to the total weight of the fluid.

16. A drilling fluid used in the presence of water, comprising cellulose nanofibrils containing at least 80% of cells with primary walls and charged with carboxylic acids or with acidic polysaccharides, a& being prepared from a dispersion of cellulose nanofibrils which have not undergone drying after they have been obtained.

17. A drilling fluid as defined in claim 1, being prepared from a cellulose nanofibril composition obtained from the dying of a nanofibril dispersion in the presence of a carboxycellulose in salt or acid form with a degree of substitution of greater than 0.95, a natural polysaccharide, or a polyol.

18. A drilling fluid as defined in claim 6, further comprising a thinning or dispersing agent in an amount of up to 1% relative to the total weight of the fluid; an oxygen scavenger in a content of up to 0.25% relative to the total weight of the fluid; a weighting compound which is an alkaline-earth metal sulphate, an alkaline-earth metal carbonate, an alkaline-earth metal silicate, an alkaline-earth metal bromide, a zinc bromide, or an iron oxide; at least one mineral colloid which is attapulgite, baryta, or bentonite; and salts.

* * * * *